United States Patent [19]

Findl et al.

[11] 4,166,455
[45] Sep. 4, 1979

[54] APPARATUS AND METHOD FOR NON-INVASIVE DETECTION OF STRICTURES IN CONDUCTIVE FLUID CONDUITS

[75] Inventors: Eugene Findl, Amityville, N.Y.; Robert J. Kurtz, Cliffside Park, N.J.

[73] Assignee: Howmedica Inc., New York, N.Y.

[21] Appl. No.: 872,035

[22] Filed: Jan. 25, 1978

[51] Int. Cl.² .............................................. A61B 5/02
[52] U.S. Cl. .................................................. 128/691
[58] Field of Search ............ 128/2 R, 2.05 F, 2.05 R, 128/2.05 S, 2.05 V, 2.05 Z, 2.05 E, 2.06 R, 2.1 E, 2.1 R, 2.1 Z; 73/194 C, 194 E

[56] References Cited

U.S. PATENT DOCUMENTS

| | | | |
|---|---|---|---|
| 3,242,729 | 3/1966 | Keller | 128/2.05 F |
| 3,641,994 | 2/1972 | Gosling et al. | 128/2.05 S |
| 3,722,504 | 3/1973 | Sawyer | 128/2.1 R |
| 3,730,171 | 5/1973 | Namon | 128/2.1 Z |

OTHER PUBLICATIONS

Jacobson et al., IEEE International Conference on Engineering in the Ocean Environment, (Seattle), 25–28, Sep. 1973, pp. 141–147.

*Primary Examiner*—William E. Kamm
*Attorney, Agent, or Firm*—Larson, Taylor and Hinds

[57] ABSTRACT

A method and apparatus are disclosed for non-invasively detecting the location of a constriction in a vessel through which a conductive fluid is flowing by externally measuring the streaming potentials generated by the flowing fluid. In an exemplary embodiment, the present invention detects the location of atherosclerotic lesions in human arteries through which the blood is being pumped in a pulsatile manner. The lesion creates a turbulent flow in the blood which in turn results in a significantly larger streaming potential being generated. The apparatus comprises two closely spaced apart, passive electrodes, which can be relatively movably mounted on a housing and a voltage detecting device, such as an oscilloscope, coupled to the electrodes.

12 Claims, 3 Drawing Figures

APPARATUS AND METHOD FOR NON-INVASIVE DETECTION OF STRICTURES IN CONDUCTIVE FLUID CONDUITS

FIELD OF THE INVENTION

The present invention relates to apparatus and a method for non-invasively determining the position of strictures in fluid conduits through which a conductive fluid is flowing. More particularly, the present invention relates to the sensing and measurement of electrical streaming potentials measured along the length of a conduit with spaced, passive electrodes and in one preferred embodiment, the present invention relates to a method and apparatus for detecting, characterizing and quantifying atherosclerotic lesions in blood vessels.

BACKGROUND OF THE INVENTION

According to the present electrokinetic theory, all electrokinetic phenomenon (e.g., streaming potential, electrophoresis, sedimentation potentials, and electroosmosis) are interrelated phenomenon and are based upon the fundamental electrochemcial concept of the "double layer." The double layer concept was first described by Helmholtz in the last half of the nineteenth century and has been modified by many others since. In essence, an electrical double layer surrounds any surface in contact with a liquid and consists generally of an immobile layer of ions next to the surface and a mobile layer of ions electrostatically in equilibrium with the ions in the immobile layer. The Encyclopedia of Electrochemistry edited by Hampell (Reinhold Publishing Corp. 1964) identified the double layer as follows.

"At any phase boundary there is always some redistribution of electrical charge because of the inhomogeneous field. This may be represented as two parallel sheets of charge of opposite sign known as a double layer. This name is retained even if the structure is more complex."

Charles Reilley in his article entitled, "Fundamentals of Electrode Processes", *Treatise on Analytical Chemistry*, edited by Kolthoff and Elving (John Wiley and Sons, Inc. 1963), Part I, Volume 4, Chapter 42, at page 2127-2129, discusses in greater detail the electrical double layer. In particular, the double layer is analogized to the assemblage of a plurality of charged layers at the liquid-solid interface.

Non-invasive measurement of internal body quantities usually involves detecting and measuring the effects the desired quantity has on the body environment around that quantity. For example, if the desired quantity to be measured is blood flow or blood velocity, it is possible to measure this quantity using the non-invasive techniques of: (1) ensonification; (2a) impedance plethysmograph, and the related approach of (2b) detecting the modulation of the amplitude of an electric signal; (3) and the generated electrical current resulting from blood (a conductive fluid) flowing through an impressed magnetic field. United States patents disclosing the foregoing techniques include the following patents arranged by the above grouping: (1) U.S. Pat. No. 3,830,223 to Beretsky et al; (2a) U.S. Pat. No. 3,835,839 to Brown and U.S. Pat. No. 3,835,840 to Mount; (2b) U.S. Pat. Nos. 3,823,706 and 3,689,393 to Davis and U.S. Pat. No. 3,131,689 to Rodler; (3) and U.S. Pat. Nos. 3,809,070, 3,759,247 and 3,659,591 to Doll et al. Each of these techniques utilize at least one pair of detecting electrodes placed on the body surface and a means for impressing an external field (e.g., (1) sound, (2) electrical or (3) magnetic) into the vicinity of the detecting electrodes or with the detecting electrodes. Other techniques use the relatively expensive and potentially hazardous conventional x-ray and related electromagnetic radiation imaging methods.

The foregoing techniques are but a few of many different approaches. Each technique and approach has its advantages and disadvantages. With respect to a method of evaluating strictures in blood vessels, such as atherosclerotic lesions, none of the aforesaid patents disclose satisfactory methods or apparatuses. Usually the electrodes are not mobile enough and are not sensitive enough so that the small change in blood flow characteristics around such a stricture can be detected. Thus there is a need for a device and a method for the detection characterization and quantification of strictures in conduits containing a flowing conductive fluid such as atherosclerotic lesions in blood vessels.

SUMMARY OF THE INVENTION

The present invention is based upon the scientific concept of the electrokinetic phenomenon known as streaming potential. Electrokinetics is the branch of electrochemistry that deals with the relative motion between a solid and a fluid moving past it. The present inventors have discovered that readily measurable electrical potentials are generated by the streaming potential phenomenon in a closed loop flow system such as the cardiovascular blood system in mammals. More particularly, it was discovered that constrictions in the arteries such as those caused by atherosclerotic lesions cause increases in the velocity of the blood. As a result, it was further discovered that the streaming potential generated in the region near the lesions is greatly increased.

Helmholtz in his treatise, Ann Physik, Liepzig 3 (7), 337, (1879) provided insights to the physical models and mathematical relationships describing the streaming potential. His mathematical relationships of streaming potential under laminar flow conditions have withstood over a century of examination and remain virtually unchanged. The relationships for circular cross-sectional flow channels in terms of pressure differential ($\Delta P$) and fluid velocity (u) for laminar flow are as follows:

$$E_S = [L_S D \zeta / 4\pi \mu k L^*] \Delta P; \text{ and}$$

$$E_S = [8 L_S D \zeta / \pi d^2 k] u;$$

where:

$E_S$ is the streaming potential $\zeta$ is the zeta potential of the electrolyte/solid interface $\mu$ is the fluid viscosity $k$ is the electrolyte conductivity $L^*$ is the distance between the pressure drop measuring points $d$ is the internal diameter of the circular fluid conduit $D$ is the dielectric constant However, no literature could be found to describe the streaming potentials in the turbulent flow region. As a result of scientific research, it was found that streaming potentials in the turbulent flow region follow the following relationship:

$$E_S = [0.0396 D \zeta \rho^{3/4} L_S / \pi \mu^{3/4} d^{5/4} k] u^{7/4}$$

where $\rho$ is the density of the fluid

It can thus be seen from the foregoing relationships for the streaming potential both in the laminar flow region and in the turbulent flow region the streaming potential is proportional to the fluid velocity and it greatly increases in the turbulent flow region, having a considerably larger magnitude than could be expected from an extrapolation of the laminar flow formula. The magnitude of the difference between the streaming potential in the turbulent flow region and the laminar flow region is surprisingly large and provides the scientific basis for the present invention whereby even low resistivity electrolytes, such as blood, generate significant electrical potentials on the order of millivolts. It was further found that these potentials could be measured external to the vessel through which the fluid was flowing if the vessel is comprised of an ionically conductive material. In particular, these potentials could be measured on the surface of the skin whereby the electrical potentials are coupled to the surface electrode by the skin of the body (the bulk resistivity of the body being approximately 1,100 ohm cm).

It is noted that previous models of the double layer lead to the false conclusion that streaming potentials cannot exist in closed loop flow systems. Closed loop streaming potentials can be readily explained by an electrical analogy. Since Kirchoff's laws of networks must apply to a closed loop system, the algebraic sum of the streaming potentials around the loop must equal zero. This leads to the conclusion that if a flow loop is symmetrical, no streaming potential will be exhibited over any segment. However, if a flow loop is non-symmetrical, for instance, a pump is located in the flow loop, the tubing diameter changes in the flow loop, or the tubing type changes in the flow loop, streaming potentials do exist.

By detecting the location of artherosclerotic lesions through the measurement of arterial streaming potentials on the surface of the skin, a simple, low-cost detection technique that can be operated by paramedical personnel has been provided. In addition, the potentially harmful results from the use of x-rays and other high energy electromagnetic radiation is avoided. Since the present invention uses a non-invasive exploratory technique, the trauma associated with traditional invasive techniques is avoided.

The method according to the present invention comprises detecting the streaming potential at a plurality of locations along the length of a vessel through which a conductive fluid is flowing, and comparing the plurality of detected streaming potentials and selecting the detected streaming potential which has the highest relative magnitude. The constriction is located in the corresponding location where the highest streaming potential was detected. In a preferred embodiment of the invention, the method comprises moving a pair of passive electrodes over the surface of the skin of a mammal under which a blood vessel having a suspected constriction is located. The electrodes sense the electrokinetic potentials generated by the flow of blood through the vessel and the constriction is located at the length of vessel producing the highest streaming potential.

Sensing apparatus according to the present invention comprises a housing, a first passive electrode mounted to said housing, and a second passive electrode mounted to the housing and closely spaced from the first passive electrode. A potential measuring means, such as an oscilloscope, is electrically connected to the first and second passive electrodes and is for measuring the potential generated therebetween.

Other advantages, features and objects of the present invention are set forth in, or apparent from, the accompanying drawings and detailed description of the presently preferred embodiment found hereinbelow.

DETAILED DESCRIPTION OF THE PRESENTLY PREFERRED EMBODIMENTS

Reference is now made to the several figures wherein like numerals designate like elements throughout the several views.

Figure 1:
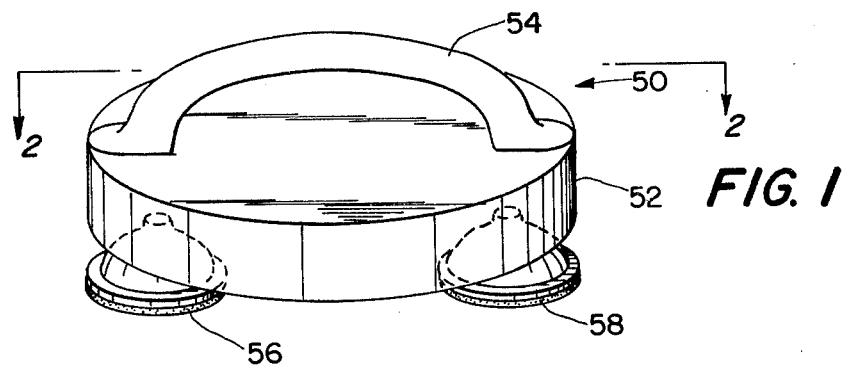
FIG. 1 is a perspective view of part of a sensor according to a presently preferred embodiment of the present invention.
Figure 2:
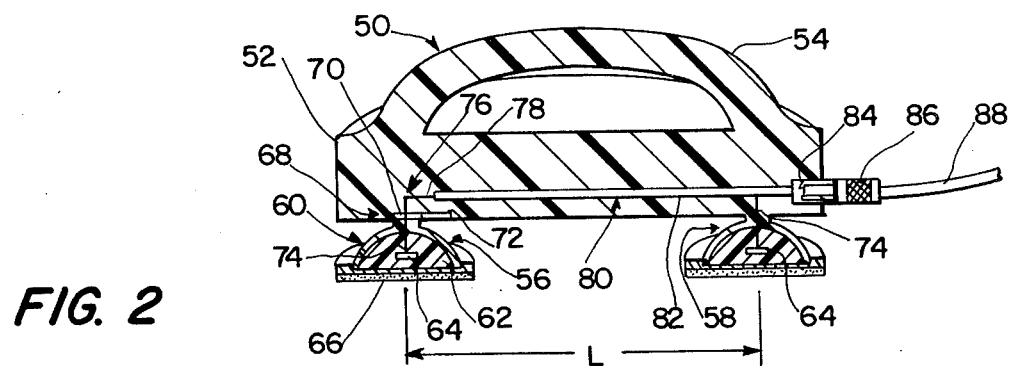
FIG. 2 is a cross-sectional view taken along line 2—2 of FIG. 1.

A sensor 50 for detecting the electrical streaming potentials is depicted in FIGS. 1 and 2. Sensor 50 comprises a housing 52 in an oval disc shape and made from an insulative material, such as a hardened, mouldable, thermoplastic resinous material. A handle 54 is attached to the upper side of housing 52 and two passive electrodes, 56 and 58 are mounted on the lower side of housing 52 spaced apart from one another. Each electrode comprises a hollow base 60 filled with a paste electrolyte 62, such as potassium chloride, an electrode pellet 64, embedded in electrolyte 62, and a covering porous membrane 66. Second electrode 58 is rigidly mounted to housing 52, whereas first electrode 56 is movably mounted to housing 52.

First electrode 56 is positionably mounted to housing 52 with mounting means 68 that can comprise, in an exemplary embodiment, a nipple 70 rigidly mounted to the top of base 60 and a slot 74 in housing 52 for slidably receiving nipple 70. A lead wire 74 is electrically connected at one end thereof to electrode pellet 64 and is connected to a sliding contact 76 at the other end thereof. Sliding contact 76, in turn, is in sliding, electrical contact with a base contact 78 which can merely be, for example, the inner conductor of a coaxial cable 80.

Coaxial cable 80 is comprised of an inner conductor 78, as mentioned above, which is electrically connected to electrode pellet 64, and an outer conductor 82 which is electrically connected through a lead wire 74 to second electrode pellet 64. The end of coaxial cable 80 terminates in a female connector or plug 84 located in the periphery of sensor housing 52. A mating jack 86 connected at the end of a coaxial connection cable 88 provides electrical coupling between sensor 50 and a measuring device.

The aforedescribed sensor 50 is but an exemplary embodiment of a sensor having two electrodes which is usable for measuring streaming potential according to the present invention. The electrode pellets 64 are preferably made of silver-silver chloride and are protected by a porous membrane which is preferably saturated with an electrolyte, thereby assuring good electrical contact between electrode pellet 64 and the skin of the body being monitored. The spacing between first and second electrodes 56 and 58 is relatively small, preferably having an order of magnitude of 5 cm, and preferably is adjustable.

Figure 3:
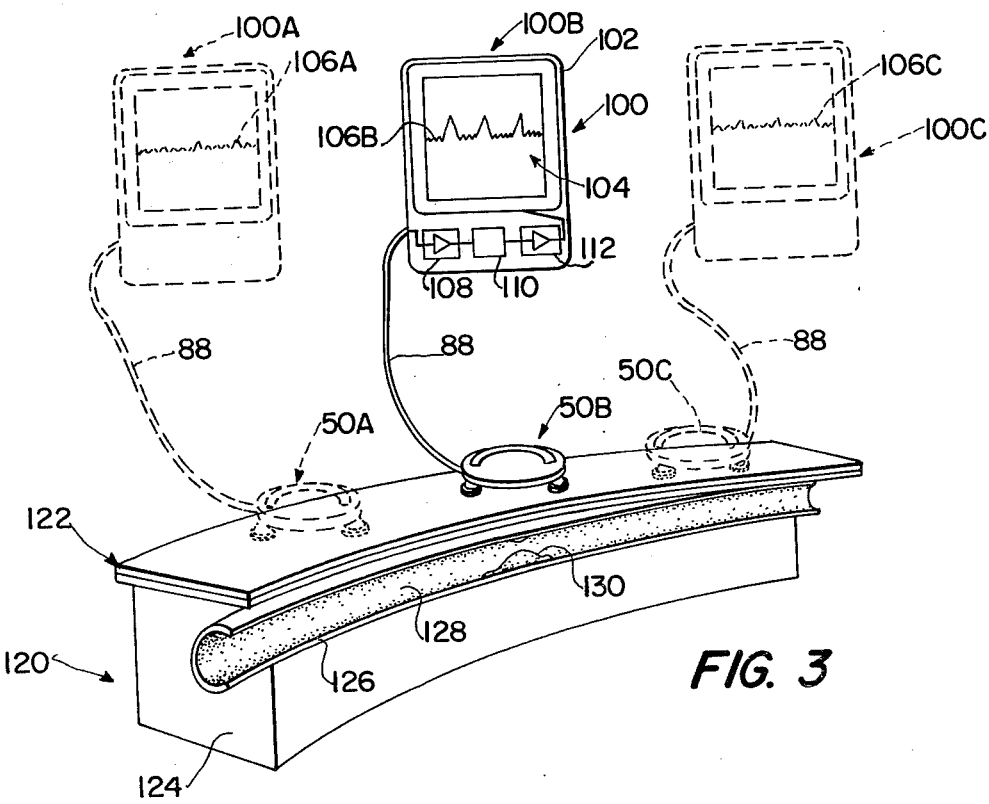
FIG. 3 is a diagrammatic representation of the scanning and pinpointing of a lesion in a blood vessel and of the detected signals.

With reference now to FIG. 3, a sensing apparatus is depicted for use in non-invasiving detecting the location of a constriction in a vessel through which a conductive fluid is flowing. The apparatus is comprised of the aforedescribed sensor 50 electrically coupled through connection cable 88 to a detector 100. Detector 100 is comprised of a housing 102 which contains a cathode ray tube (CRT) 104 having a display 106 thereon. Detector 100 also contains a conventional AC amplifier 108, the input of which is electrically coupled with the other end of connection cable 88. The output of amplifier 108 is coupled to a conventional filter network 110, which can be an active or a passive filter, for minimizing noise and artifact signals. The output of filter 110 is coupled to the input of a second amplifier 112, which is also of conventional design, for removing the DC bias potentials. The output of second amplifier 112 is electrically coupled to CRT 104.

Also schematically shown in FIG. 3 is a portion of a human body 120 to be non-invasively scanned with sensor 50. Body 120 is comprised of skin layers 122 and subcutaneous tissue 124 having an artery 126 extending therethrough. Artery 126 is an ionically conductive vessel through which blood 128, which is a conductive fluid, flows in a pulsatile manner. An atherosclerotic lesion 130 is located on the inside of artery 126, thereby providing an internal constriction of the vessel. As a result of lesion 130, blood 128 has a generally laminar flow upstream and downstream of lesion 130 and a turbulent flow in the vicinity of lesion 130. Detector 100 is shown in three positions, 100A, 100B, and 100C, for measuring the streaming potential generated by blood 128 flowing through artery 126 at a location upstream, at, and downstream of lesion 130, respectively. A close approximation of the detected signal is depicted on corresponding displays 106A, 106B and 106C.

According to the present invention, the measurement of absolute values of arterial streaming potentials on the surface of the skin is unnecessary for the detection of atherosclerotic lesions. Since the electrolyte, that is the blood, flowing in the arterial system is pulsatile, the generated potentials are pulsatile direct current, DC, superimposed on a background DC level of an undeterminant and variable origin. The DC background presents an undesirable and probably artifactual source of error in many instances. Therefore, elimination of the undesired DC error signal is accomplished using conventional AC amplification techniques. Such amplification with amplifiers 108 and 112, together with a noise filter 110, removes nearly all of the DC bias potentials except for the pulsatile signals in the frequency range of interest.

Another potential source of error in detecting streaming potentials is the EKG signal generated by the heart and which, it is theorized, can be at least partially due to streaming potentials. Therefore, it is preferable to blank out any signal received during the P and QRS portions of the EKG signal. Unfortunately, the T wave portion of the EKG signal cannot be similarly eliminated. However, this potential source of error can be minimized by the operator if a continuous chart is made of the detected streaming potentials.

FIG. 3 also graphically demonstrates the method according to the present invention. A sensor 50 is electrically coupled to a detector 100 with a connection cable 88 and is then placed in physical and electrical contact with the skin of a mammal, for example, a human being, over the vessel to be monitored. Detector 100 is a voltage detector, which preferably is an oscilloscope, and is used to measure the voltage difference between electrodes 56. A display of the generated streaming potential, such as display 106A of detector 100A, is shown in phantom. After a sufficient signal has been recorded, and preferably permanently recorded on a paper tape with conventional apparatus not shown, sensor 50 is moved along a body 120 over the vessel 126 to a second location depicted at 50B. Since this location is directly above lesion 130, the display 106B is much larger. Finally, sensor 50 is moved to a third location shown in phantom at 50C with the resulting display 106C being depicted. Sensor 50 which has the largest signal being generated, is then returned to the location, shown at 50B, and the distance between first and second electrodes 56 and 58 is reduced in order to pinpoint the narrowed lumen region. In this manner, the exact location of lesion 130 can be non-invasively detected.

The present invention has been described hereinabove with a presently preferred, exemplary embodiment. As described, the present invention provides a method and apparatus for accurately detecting the location of a constriction in an ionically conductive vessel through which a conductive fluid is flowing. The instrumentation and sensor costs of the present invention are relatively low and the method can be performed by paramedical personnel with very little additional training. With the use of the present method and apparatus, there is no significant patient trauma and the entire screening time can be as small as 15 minutes. Because the instrumentation is small, the present apparatus is highly portable.

However, the present invention should not be construed to be limited to the detection of atherosclerotic lesions in a human being since the present method and apparatus could equally be employed with any ionically conductive conduit or vessel having a conductive fluid flowing therethrough. Therefore, although the invention has been described in detail with respect to exemplary embodiments thereof, it will be understood by those of ordinary skill in the art that variations and modifications may be effected within the scope and spirit of the invention.

We claim:

1. A method for detecting the location of a constriction in an ionically conductive vessel through which a conductive fluid is flowing comprising
   detecting the streaming potential at a plurality of locations along the length of the vessel; and
   comparing the plurality of detected streaming potentials, and selecting the detected streaming potential which has the highest relative magnitude, said constriction being located in the corresponding location where said highest streaming potential was detected.

2. The method as claimed in claim 1 wherein two spaced apart, passive electrodes are used to detect the streaming potential along a plurality of lengths of the vessel.

3. The method as claimed in claim 2 wherein the spacing between said electrodes is constant for each of said plurality of locations.

4. The method as claimed in claim 2 wherein said spacing is relatively small compared with the length of the vessel.

5. The method as claimed in claim 4 wherein said spacing is in the order of magnitude of 5 centimeters.

6. The method as claimed in claim 2 wherein said spacing between said electrodes is initially set at a first larger length and wherein said method further comprises reducing said spacing to pinpoint the location of said constriction.

7. The method as claimed in claim 1 wherein the fluid has a pulsatile flow through the vessel.

8. The method as claimed in claim 7 wherein said constriction is located at the place of highest turbulence in the fluid flow by detecting at said location the generated pulsatile direct current potentials.

9. The method as claimed in claim 8 and further comprising amplifying said detected potential, filtering out noise from said detected potential, and removing any direct current bias potential from said detected potential.

10. The method as claimed in claim 1 wherein the location of atherosclerotic lesions are detected in the arteriovascular system of a body.

11. Sensing apparatus for use in non-invasively detecting the location of a constriction in an ionically conductive vessel through which a conductive fluid is flowing by detecting the streaming potential generated by the flowing fluid, the apparatus comprising:
   a housing;
   a first passive electrode mounted to said housing;
   a second passive electrode mounted to said housing closely spaced from said first passive electrode, and
   potential measuring means electrically connected to said first and second passive electrode for measuring the potential generated therebetween.

12. A sensor as claimed in claim 11 wherein at least one of said first and second electrodes is positionably mounted on said housing such that the spacing between said first and second electrodes can be varied.

* * * * *